United States Patent [19]

Amemiya et al.

[11] Patent Number: 5,011,589
[45] Date of Patent: Apr. 30, 1991

[54] SOLUTION COMPONENT SENSOR DEVICE

[75] Inventors: Isao Amemiya; Tadashi Sakai, both of Yokohama; Shigeki Uno, Tokyo, all of Japan

[73] Assignee: Kabushiki Kaisha Toshiba, Kawasaki, Japan

[21] Appl. No.: 411,112

[22] Filed: Sep. 22, 1989

[30] Foreign Application Priority Data

Sep. 30, 1988 [JP] Japan .................... 63-246442

[51] Int. Cl.$^5$ .................. G01N 27/333; G01N 27/414
[52] U.S. Cl. .................................. 204/416; 204/419; 204/435
[58] Field of Search ............... 204/416, 418, 419, 435

[56] References Cited

U.S. PATENT DOCUMENTS

| | | | |
|---|---|---|---|
| 2,157,180 | 5/1939 | Little ..................................... | 204/197 |
| 4,020,830 | 5/1977 | Johnson et al. ..................... | 204/418 |
| 4,269,682 | 5/1981 | Yano et al. .......................... | 204/418 |
| 4,791,465 | 12/1988 | Sakai et al. . | |

FOREIGN PATENT DOCUMENTS

| | | |
|---|---|---|
| 0155725 | 9/1985 | European Pat. Off. . |
| 0258951 | 3/1988 | European Pat. Off. . |
| 57-793247 | 6/1982 | Japan . |
| 58-25221 | 5/1983 | Japan . |
| 2017400 | 10/1979 | United Kingdom . |

OTHER PUBLICATIONS

Medical & Biological Eng., vol. 18, No. 6, Feb. 1980 pp. 741-745, Stevenage, Herts, GB; K. Shimada et al.: "Application of Catheter-tip i.s.f.e.t. for continuous in vivo measurement" * En entier * .

Primary Examiner—T. Tung
Attorney, Agent, or Firm—Oblon, Spivak, McClelland, Maier & Neustadt

[57] ABSTRACT

Disclosed is a sensor device for detecting a specified chemical component of a solution. The sensor device includes an electrode for generating a potential corresponding to a concentration of a specified component of a solution, a reference electrode including a insulated-gate FET having a film insensitive to the component of the solution formed on the gate region, and an electrode for detecting a potential difference between the potential generating electrode and the reference electrode. The insensitive film included in the reference electrode contains a siloxane copolymer.

9 Claims, 5 Drawing Sheets

SOLUTION COMPONENT SENSOR DEVICE

BACKGROUND OF THE INVENTION

1. Field of the Invention

The present invention relates to a sensor device for detecting a specified chemical component in a solution and, more particularly, to such a sensor device having a reference FET which exhibits a constant potential with respect to a solution without responding to the chemical components such as ions in the solution.

2. Description of the Related Art

Ion-sensitive electrodes (ISEs) have been widely used for detecting the ion concentration of a solution. Recently demands for miniature sensors capable of detecting the concentration of a specified ion species in a very small region are on the increase in the field of, for example, clinical medicine. In an ISE using, for example, a glass electrode, the glass film inherently has a high resistance as high as about 10 MΩ. In order to use such an electrode type sensor in detecting the components of a solution, it is necessary to use an amplifier having a high input impedance. Also, where the sensor of this type is miniaturized, the resistance of the glass film is increased. It follows that a miniature electrode type sensor tends to invite an external noise, leading to a delay in the response speed. Under the circumstances, an ion sensitive FET (ISFET) in which an ion sensitive film is formed on the gate region of an insulated-gate FET is getting attentions nowadays. Since the ISFET exhibits an impedance converting function, it permits the miniaturization, making it possible to overcome the above-noted problems inherent in the electrode type sensor.

In the case of using an ISFET, it is also necessary to use a reference electrode which provides a basis of the relative potential value. Naturally, it is absolutely necessary to miniaturize the reference electrode in the case of miniaturizing a sensor using an ISFET. A reference electrode of a half cell type, in which a single electrode such as a calomel electrode or silver/silver chloride electrode is in contact with an electrolyte solution, is known in the art. However, the electrode of such a half cell type unavoidably necessitates a liquid junction, with the result that, when the electrode is miniaturized, the resistance is increased in the liquid junction, leading to an unstable output potential. In addition, the electrode of a half cell type tends to give rise to leakage of the electrolyte solution from the liquid junction portion. The leakage of the electrolyte solution results in difficulties such as an increased obstructive ion concentration and an increased ionic strength in the step of detecting the ion species in a very small region, making it impossible to detect ion concentration accurately. Further, it is impossible to markedy diminish the amount of the electrolyte solution in view of the leakage. This also gives a restriction to miniaturization of the reference electrode.

Under the circumstances, a FET type reference electrode (reference FET), in which the gate region of an insulated-gate FET is covered with a non-porous film formed of a hydrophobic polymer is described in Published Examined Japanese Patent Application No. 58-25221. The reference FET of this type utilizes the fact that since ion dissociating groups such as hydroxyl groups are not present on the surface of the hydrophobic polymer film formed on the gate insulation film, the polymer film does not respond to specified ion specing, giving a constant gate potential to the reference FET. When the ion concentration of a solution is actually detected by using the reference electrode of this type, an ISFET and an inactive metal electrode serving to give a predetermined potential to a solution are dipped in the solution together with the reference electrode so as to measure the potential difference between the ISFET and the reference FET.

It has been found, however, that not all the hydrophobic polymer film are suitable for use as an insensitive film of a reference FET. For example, hydrophobic polymer films insensitive to specified ion species but sensitive to electrostatic properties of the solution such as the ionic strength are not suitable for use as an insensitive film of the reference FET. If the hydrophobic polymer film is sensitive to the ionic strength of a solution, the potential of the reference FET is not maintained constant. It follows that a sensor device using such a hydrophobic polymer film is incapable of accurately detecting the concentration of the specified ions.

As described above, the prior art reference FET is disadvantageous in that the it is affected by, in particular, the ionic strength of the solution, failing to maintain a constant potential.

SUMMARY OF THE INVENTION

An object of the present invention is to provide a sensor device for detecting a specified chemical component of a solution using a reference FET which is substantially unaffected not only by the concentration of ionic component but also by the ionic strength of the solution so as to exhibit a constant output potential.

Another object is to provide a sensor device for detecting a specified chemical component of a solution which permits readily detecting the components of a solution within a substance capable of retaining water such as soil and rock wool.

According to a first aspect of the present invention, there is provided a sensor device for detecting a specified chemical component of a solution, comprising:

means for generating a potential corresponding to a concentration of a specified component of a solution;

reference means including an insulated-gate FET having a film insensitive to the component of the solution formed on its gate region, said insensitive film comprising a siloxane copolymer; and means for detecting a potential difference between the potential generating means and the reference means.

According to a second aspect of the present invention, there is provided a sensor device for detecting a specified chemical component of a solution, comprising:

(A) a sensor body having first and second end portions, said sensor body including;
  (a) a semiconductor substrate,
  (b) a first insulated-gate FET formed on the semiconductor substrate, said FET having a film sensitive to a specified ion component formed on its gate region,
  (c) a second insulated-gate FET formed on the semiconductor substrate, said FET having a film insensitive to ion components formed on its gate region, and
  (d) means for detecting a potential difference between the first and second FETs;
(B) a support member having first and second end portions and serving to support said sensor body such that the first end portion of the sensor body extends from the first end portion of said support member;

(C) a reinforcing member having first and second end portions, said first end portion of the reinforcing member extending from said support member over the first end portion of the sensor body and forming a tapered portion; and (D) a sealing member for sealing the sensor body and the reinforcing member except for the gate portions of the first and second FETs.

DETAILED DESCRIPTION OF THE PREFERRED EMBODIMENTS

The sensor device of the present invention comprises a reference FET which includes a film insensitive to the chemical components of a solution. In the first aspect of the present invention, the insensitive film is required not to be affected greatly by the ion concentration and ionic strength so as to exhibit a constant surface potential difference. In the present invention, the sensitivities to pH, which indicates the ion concentration, and to ionic strength are used as parameters in selecting the material of the insensitive film included in the reference FET.

Table 1 shows the sensitivities to pH and to ionic strength of reference FE using various insensitive films.

TABLE 1

| Film Material | Sensitivity to pH (mV/pH) | Sensitivity to ionic strength (mV/decade) |
| --- | --- | --- |
| Polyethylene | 3 | 35 |
| Fluoro resin (PTFE) | 1 | 53 |
| Silicone resin | 1 | 35 |
| Acrylic resin (PMMA) | 47 | — |
| Siloxane-MMA Graft copolymer | <1 | 12 |

As apparent from Table 1, the siloxane-MMA (methyl methacrylate) graft copolymer, which is one of siloxane copolymers, is low in sensitivity to both pH and ionic strength, when used as the insensitive film of the reference FET. On the other hand, the reference FETs having polyethylene resin, fluoro resin (polytetrafluoroethylene), and silicone resin are largely affected by the ionic strength of the solution. Thus, the output potential of these reference FETs greatly vary if the ionic strength of the tested solutions differ, leading to a large measurement error, even when the pH values of the solution are the same. Therefore, when polyethylene, fluororesin, or silicone resin is used as an insensitive film for the reference FET, strong electrolyte such as ionic strength conditioner not involving in ion measurement must be added to the solution to be tested so as to render the ionic strength constant. Further, polymethyl methacrylate (PMMA) is not suitable as an insensitive film for the reference FET since it gives rise to changes of the output potential in response to changes of pH value of the solutions.

Based on these experiments, the present inventors have found that siloxane copolymers, i.e., copolymers of siloxane with a comonomer or comonomers, are particularly suitable as a material forming the insensitive film for the reference FET.

Figure 1:
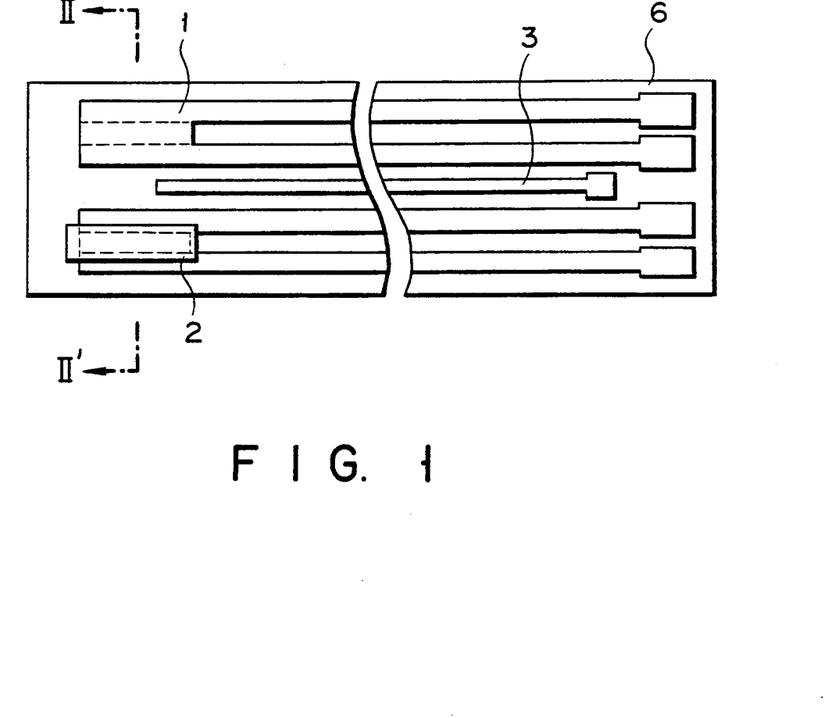
FIG. 1 is a plan view showing a FET type pH sensor device according to one embodiment of the present invention.
Figure 2:
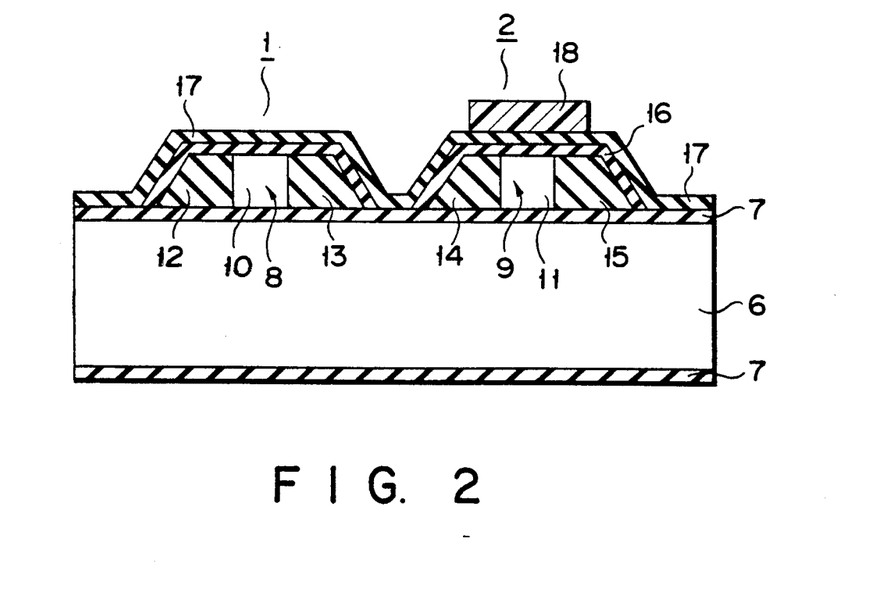
FIG. 2 is a cross sectional view along the line II—II' shown in FIG. 1.

FIG. 1 is a plan view showing a FET type pH sensor device according to on embodiment of the present invention, and FIG. 2 is a cross sectional view along the line II—II' shown in FIG. 1. In this embodiment, the pH sensor device is of SIS (Silicon-Insulator-Silicon) structure, and an ISFET 1 and a reference FET 2 are integrally formed on a silicon substrate 6.

As shown in FIG. 2, a first SiO$_2$ film 7 is formed on each of the upper and lower surfaces of the silicon substrate 6. Silicon layers 8 and 9 are formed island-like on the first SiO$_2$ film 7. A gate region 10, and first and second diffusion layers 12, 13, which are arranged on the both side of the gate region 10, are formed in the silicon layer 8. Likewise, a gate region 11, and first and second diffusion layers 14, 15, which are arranged on the both side of the gate region 11, are formed in the silicon layer 9. Each of the first diffusion layers 12 and 14 acts as a source. Each of the second diffusion layers 13, 15 acts as a drain. Of course, it is possible to allow the first diffusion layers to act a drains and the second diffusion layers to act as sources.

The first and second diffusion layers can be formed by selectively introducing an impurity element into the silicon layers 8, 9 by means of ion implantation with the gate regions 10, 11 being masked. After formation of these diffusion layers, a second SiO$_2$ film 16 acting as a gate insulation film is formed to cover the silicon layers 8 and 9 as well as these diffusion layers. Further, a SiNx film 17 which acts as a passivation layer and a film sensitive to H+ ions, is formed to cover the SiO2 film 16. As seen from FIG. 2, the SiNx film 17, also covers the exposed surface of the first SiO2 film 7 on which the FETs are formed. In this embodiment, the SiNx film 17 is formed by chemical vapor deposition (CVD). A film 18 of a siloxane copolymer, which is insensitive to the solution component, is formed on a portion of the film 17 which corresponds to the gate region 11 of the insulated-gate FET 2 including the silicon layer 9, while the film 17 over the gate region 10 of the insulated-gate FET 1 formed in the silicon layer 8 remains exposed. Thus, FET 1 acts as an ISFET, while the FET 2 acts as a reference FET. Further, a Au electrode 3 is formed between these FETs on the substrate 6 as an inactive electrode serving to give a potential to a solution as seen from FIG. 1. The Au electrode 3 is formed on a Ti electrode.

The siloxane monomers include dimethyl siloxane, diphenyl siloxane and the like.

It is desirable to use nonionic monomers as comonomers forming the siloxane copolymer together with siloxane monomers. Such nonionic monomers include, for example, olefinic monomers such as ethylene and propylene, halogenated olefinic monomers such as vinyl chloride and tetrafluoroethylene, diene type monomers such as butadiene and isoprene, and other nonionic monomers such as styrene and methyl methacrylate.

The copolymer should desirably be of the type that, when formed as an insensitive film, the siloxane groups appear on the film surface. Particularly desirable is a graft copolymer in which the siloxane groups form side chains grafted on the main chain of the copolymer. In this case, the comonomer forming the main chain of the graft copolymer should exhibit a satisfactory strength as a substrate for the siloxane side chains. In other words, the comonomer should exhibit a strength high enough to impart a sufficient strength to the film formed of the copolymer. The nonionic monomers quoted above fully meet these conditions.

Figure 4:
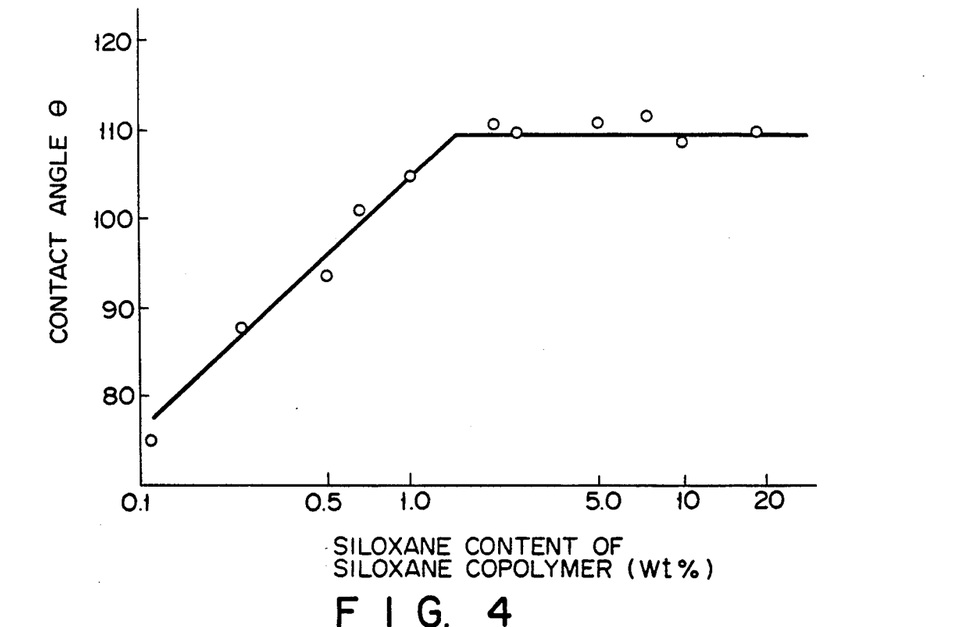
FIG. 4 is a graph showing the relationship between the contact angle with water of a siloxane copolymer and the siloxane group content of the copolymer, said copolymer consisting of siloxane monomer and another monomer.

The siloxane copolymer should desirably contain at least 1.5% by weight of the siloxane groups. In this case, the contact angle $\theta$ of the copolymer with water becomes substantially equal to that of a silicone resin and constant as shown in FIG. 4. In addition, in this amount of siloxane groups, the siloxane side chains fully govern the surface properties of the film. Therefore, the comonomers forming the main chain are not particularly limited in the graft copolymer containing at least 1.5% by weight of siloxane groups except for the above-mentioned criteria.

The copolymer film 18 can be formed by, for example, coating the gate region of the FET with a solution of the copolymer, followed by drying in air at room temperature for about one hour.

Figure 3:
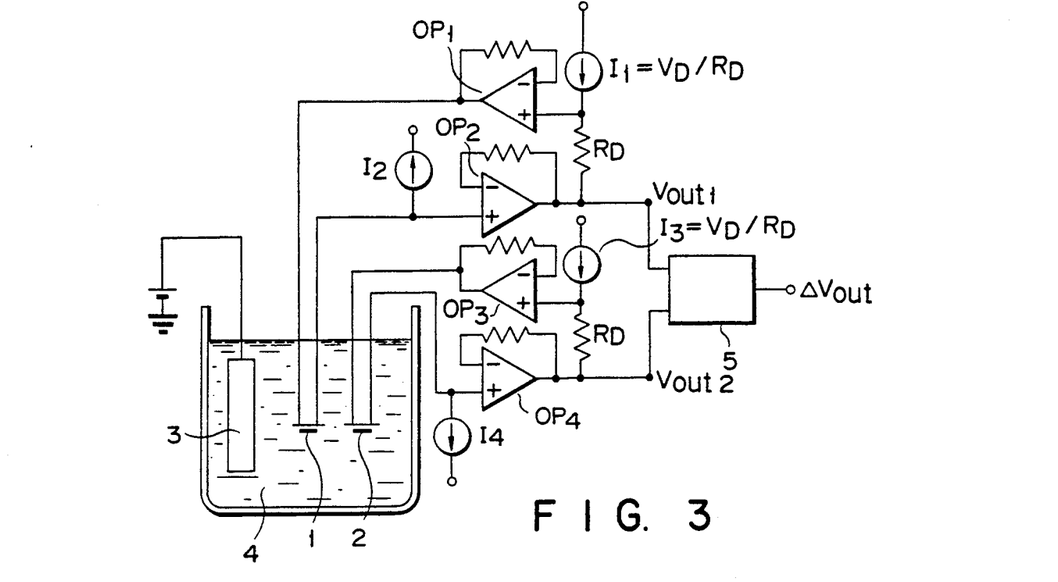
FIG. 3 shows a pH measuring device using a sensor device of the present invention.

FIG. 3 is circuit diagram showing how the pH sensor device described above is used for detecting the hydrogen ion concentration of the solution. In the embodiment, the ISFET 1, reference FET 2 and the Au electrode 3 are integrally formed as described previously, though these elements are separately shown in FIG. 3 for the sake of convenience. As a matter of fact, the sensor circuit can be formed even if these elements are independently formed as shown in FIG. 3.

As shown in the drawing, the ISFET 1, the reference FET 2 and the Au electrode 3 are dipped in an aqueous solution 4 to be tested. A predetermined potential is given by the Au electrode 3 to the solution 4. Each of the ISFET 1 and the reference FET 2 forms a source follower circuit, with the result that the outputs corresponding to the gate potentials are taken out as the output $V_{out}1$ and $V_{out}2$, respectively. To be more specific, a current source $I_1$ and a resistor $R_D$ serve to provide a constant voltage $V_D$ between the drain and source of the ISFET 1 via an operation amplifier $OP_1$. Then, a constant drain current is allowed to flow between the drain and the source by a constant current source $I_2$ disposed on the side of the source. It follows that a change in the gate potential of the ISFET 1 causes a change in the drain current flowing between the drain and the source. This brings about a change in the source potential. The change in the source potential is taken out as the output $V_{out}1$ via an operation amplifier $OP_2$. The circuit on the side of the reference FET 2 is similarly constructed. The difference between the outputs $V_{out}1$ and $V_{out}2$ is processed by a differential amplifier 5. The output of the differential amplifier 5 denotes a hydrogen ion concentration.

The pH measuring device constructed as described above was found to exhibit a pH sensitivity of about 58 mV/pH in the pH range of 2 to 10. In this case, the pH sensitivity of the reference FET was as low as 1 mV/pH or less. As a result, the high pH sensitivity of the SiNx film was reflected as it was when the reference FET 2 and the ISFET 1 were differentially operated, making it possible to obtain a high pH sensitively of the device.

As described previously, the siloxane copolymer film formed in the gate region of the reference FET has substantially no dissociating group on the surface. As a result, when the reference FET is dipped in a solution to be tested, the surface potential difference of the copolymer film is not affected greatly by the individual ion concentration of components and the ionic strength of the solution. Thus, the reference FET can produce a constant output. It follows that the concentration of the desired component of the solution can be stably detected by the differential operation of the reference FET and the ISFET.

Figure 5:
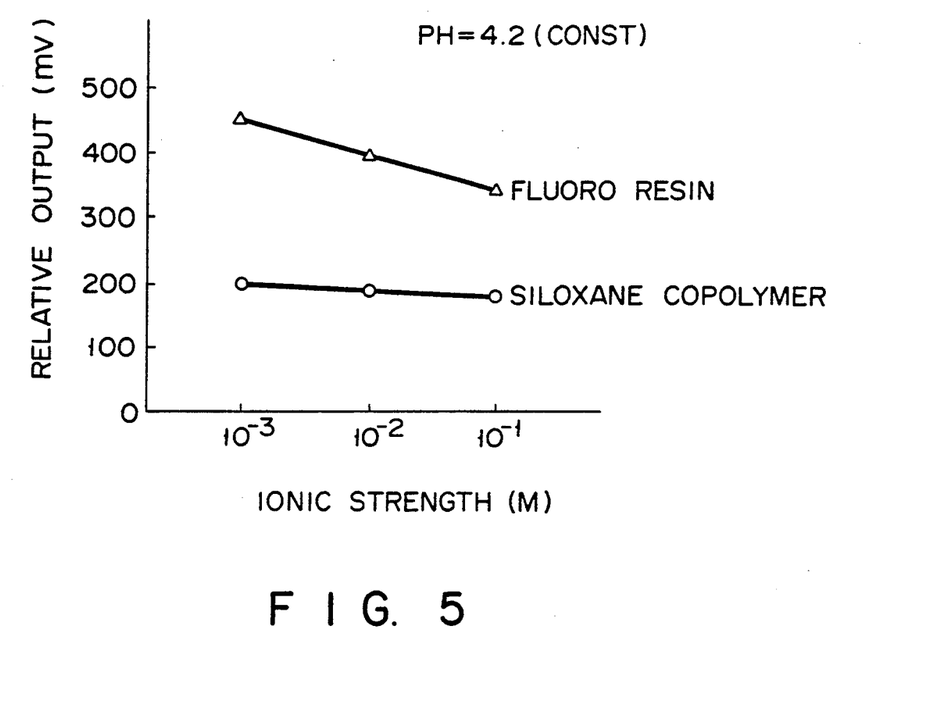
FIG. 5 is a graph showing the dependence characteristics on ionic strength of FET type pH sensors using a reference FET of the present invention and using a comparative reference FET.

FIG. 5 shows data showing the effectiveness of the reference FET used in the present invention. The data shown in FIG. 5, i.e., dependence characteristics on the ionic strength of the FET type pH sensor device, obtained when measured under a constant pH condition. For comparison, FIG. 5 also shows cases where the insensitive film of the reference FET was formed of a fluoro resin. As apparent from FIG. 5, the output potential remains substantially constant regardless of wide changes in the ionic strength in the case where the insensitive film is formed of a siloxane copolymer. On the other hand, the output potential is greatly varied with the change in the ionic strength, where the insensitive film is formed of a fluoro resin, resulting in failure to measure the pH value with a high reliability. It should be noted that, where an insensitive film is formed of the fluoro resin, it is necessary to add the strong electrolyte salt, not involving in the measurement, such as ionic strength conditioner to the tested solution so as to maintain a constant ionic strength. This is inconvenient in the case where the amount of the solution is very small, or in the case of an in situ measurement. In the case of using a siloxane copolymer film as in the present invention, however, a stable measurement can be achieved without such a treatment.

Figure 6:
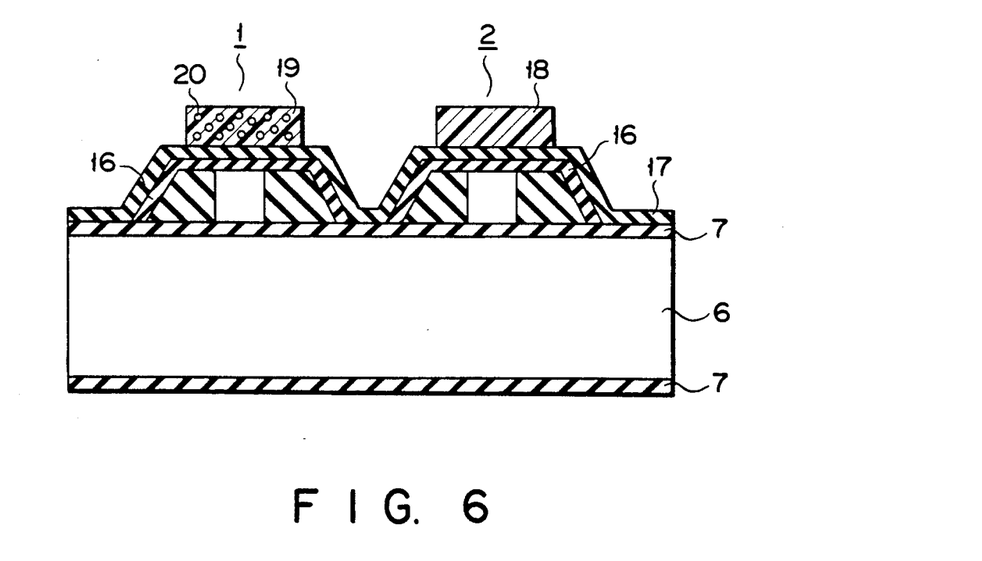
FIG. 6 shows a FET type sensor device for detecting a nitrate ion concentration according to another embodiment of the present invention.

FIG. 6 shows a nitrate ion sensor device according to another embodiment of the present invention. The reference numerals common with FIGS. 1 and 2 denote the same members of the sensor and, thus, description thereof is omitted. In the embodiment of FIG. 6, a siloxane copolymer as described above is used as a binder of the nitrate ion-sensitive substance used in the ISFET 1. To be more specific, a film 19 formed over the gate region of the ISFET 1 consists of a siloxane copolymer-based material containing 40% by weight of nitron nitrate 20, which is a powdery material sensitive to the nitrate ion The film 19 sensitive to the nitrate ion is formed by coating the gate region of the ISFET 1 with the siloxane copolymer-based material noted above, followed by drying the coating in air at room temperature for one hour. Further, a Au electrode serving to impart a potential to a solution is integrally formed on the substrate, as in the embodiment shown in FIGS. 1 and 2.

For evaluating the performance of the sensor device shown in FIG. 6, the ISFET 1 and the reference FET 2 were differentially operated as in the embodiment shown in FIGS. 1 and 2, with the result that the sensitivity to the nitrate ion concentration was 50 mV/pNO$_3$. Also, the embodiment of FIG. 6 was found substantially equal to the embodiment of FIGS. 1 and 2 in the temperature characteristics and in the change with time in performance of the ISFET 1 and the reference FET 2. Naturally, the differential output between the ISFET 1 and the reference FET 2 was highly stable in the embodiment of FIG. 6.

In the embodiment of FIG. 6, the film 19 is formed of a siloxane-based copolymer containing a powdery material sensitive to the nitrate ion. However, it is possible to use a material sensitive to a specific ion other than the nitrate ion in place of the powder material sensitive to the nitrate ion. In this case, the sensor device permits measuring the concentration of the specified ion.

Figure 7:
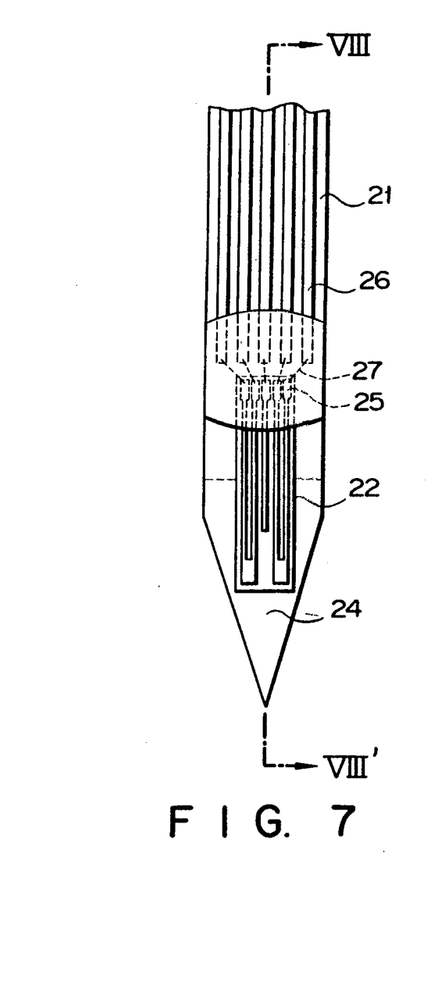
FIG. 7 is a plan view showing an example of actually mounting a probe-like FET type solution component sensor of the present invention.
Figure 8:
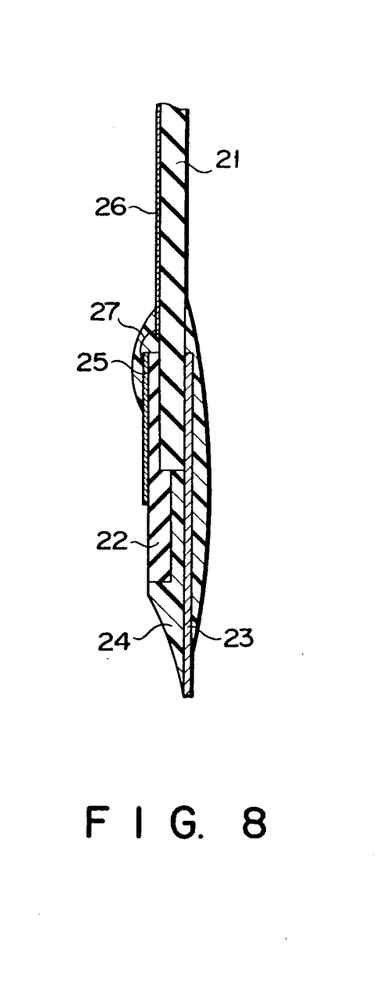
FIG. 8 is a cross sectional view along the line VIII—VIII' shown in FIG. 7.

FIGS. 7 and 8 collectively show a probe-like sensor device including a solution component sensor device of the present invention. A FET type solution component sensor body 22 included in the device shown in the drawings is provided by, for example, the pH sensor device shown in FIGS. 1 and 2 or the nitrate ion concentration sensor device shown in FIG. 6. The sensor body 22 is fixed by an adhesive to one surface of a supporting substrate 21 formed of, for example, glass epoxy. Terminals 25 on the sensor body 22 are connected to lead wires 26 extending along one surface of the supporting substrate 21 by bonding wires 27, respectively. On the other hand, a tapered reinforcing metal plate 23 formed of, for example, SUS is mounted to the back surface of the supporting substrate 21. Further, the side surface of the sensor body 22, the clearance between the sensor body 22 and the reinforcing metal plate 23, and the wiring portion are sealed by a resin layer 24. Thus, in the probe-like solution component sensor device shown in the drawings, only the required portion of the sensor body 22 including the gate portions is exposed to the outside. Incidentally, it is possible for the supporting substrate 21 to be tapered so as to enable the supporting substrate 21 to perform the function of the reinforcing metal plate.

In a probe-like sensor device having an integrated reinforcing metal plate with a tapered end as described above, the tapered end portion of the reinforcing member assures a stable contact of the sensing portion of the device with a water-retaining substance such as rock wool or soil when the sensor body 22 is inserted into such a substance. Thus, the solution component in the water-retaining substance can be readily detected under a stable output single. Also, the tapered shape of the reinforcing metal plate protects the sensor body from direct application of external force. In other words, the probe-like solution component sensor device substantially exhibits an improved mechanical strength. Further, the measured value of the sensor is made more accurate because the external force is not directly applied to the sensor body.

Figure 9:
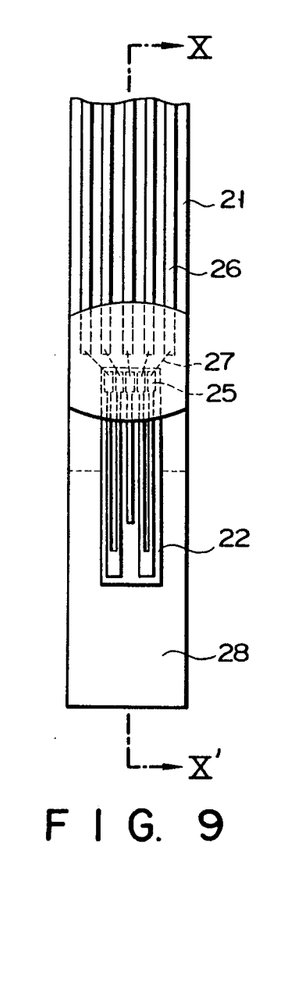
FIG. 9 is a plan view showing an example of actually mounting a comparative probe-like FET type solution component sensor.
Figure 10:
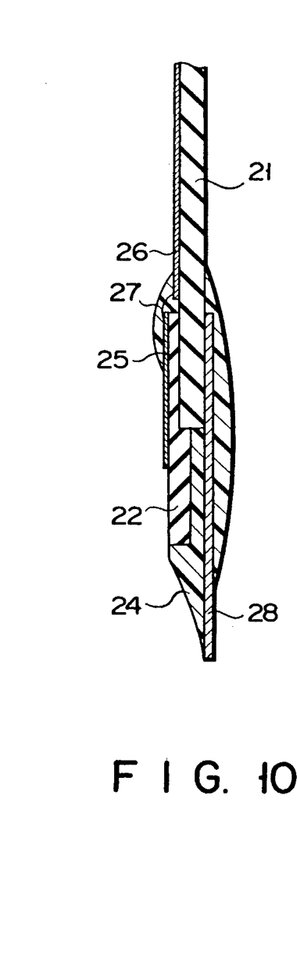
FIG. 10 is a cross sectional view along the line X—X' shown in FIG. 9.
Figure 11:
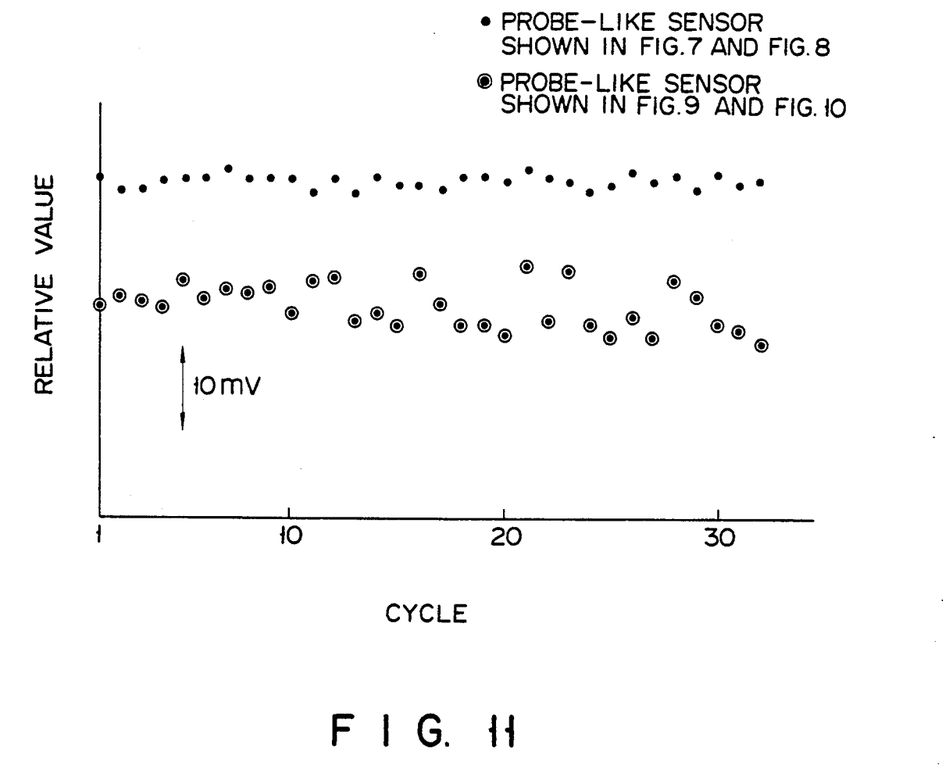
FIG. 11 is a graph showing the scattering of the measured values with respect to a probe-like FET type solution component sensor of the present invention and a conventional sensor, obtained when these sensors are repeatedly inserted into a water-retaining substance.

FIG. 11 shows the scattering of the measured value obtained by the probe-like solution component sensor device of the present invention, when the sensor is repeatedly inserted into a water-retaining substance. For comparison, also shown in FIG. 11 is the scattering of the measured values obtained by a probe-like solution component sensor device constructed as shown in FIGS. 9 and 10. A reinforcing metal plate 28 having a rectangular shaped end is used in the sensor device shown in FIGS. 9 and 10.

As apparent from FIG. 11, the probe-like solution component sensor device of the present invention is low in the scattering of the measured values, making it possible to measure stably the concentration of the desired solution component. Incidentally, the scattering of the measured values was less than $\pm 1.5$ mV in the sensor device of the present invention. On the other hand, the sensor device shown in FIGS. 9 and 10 is high in the scattering of the measured values, and the scattering of the measured values in less than $\pm 5.0$ mV.

In the embodiment shown in FIGS. 7 and 8, the insensitive film of the reference FE included in the sensor body is formed of a siloxane copolymer, making it possible to measure accurately the concentration of the desired ions.

In the embodiments described above, the reference FET is used in combination with an ISFET. However, it is also possible in the present invention to use the reference FET in combination with an electrode other than an ISFET. Even in this case, it is possible to measure accurately the concentration of a desired component of a solution.

As described above in detail, the solution component sensor of the present invention comprises a reference FET which includes a siloxane copolymer as a film insensitive to the solution component. The particular construction makes it possible to measure stably the concentration of a desired solution component, since it is not affected by the concentration of the other components with only a slight influence of the ionic strength.

What is claimed is:

1. A sensor device for detecting a specified chemical component of a solution, comprising:
   means for generating a potential corresponding to a concentration of a specified component of a solution;
   reference means including an insulated-gate FET having a film insensitive to said component of the solution formed on the gate region, said insensitive film comprising a graft copolymer of a siloxane monomer and a comonomer other than a siloxane monomer which contains at least 1.5% by weight of siloxane groups; and
   means for detecting a potential difference between the potential generating means and the reference means.

2. The sensor device according to claim 1, wherein the means for generating a potential corresponding to a concentration of a specified component of a solution is provided by an insulated-gate FET which includes a film sensitive to a specified component of the solution, said sensitive film being formed on the gate region of said FET.

3. The sensor device according to claim 2, wherein the film sensitive to a specified component of the solution contains a copolymer of a siloxane monomer and at least one comonomer, and a substance sensitive to said specified component of the solution.

4. The sensor device according to claim 1, wherein the comonomer is a nonionic monomer.

5. The sensor device according to claim 1, wherein the means for generating a potential difference comprises a comparator which is electrically connected to the means for generating a potential and to the reference means so as to generate an output signal representing the amount of the specified component of the solution on the basis of the difference between the potential signal generated by the means for generating a potential and the potential signal obtained by the reference means.

6. A sensor device for detecting a specified chemical component of a solution, comprising:
(A) a sensor body having first and second end portions, said sensor body including;
 (a) a semiconductor substrate,
 (b) a first insulated-gate FET formed on the semiconductor substrate, said FET having a film sensitive to a specified ion component formed on the gate region,
 (c) a second insulated-gate FET formed on the semiconductor substrate, said FET having a film insensitive to ion components formed on the gate region, and
 (d) means for detecting a potential difference between the first and second FETs;
(B) a support member having first and second end portions and serving to support said sensor body such that the first end portion of the sensor body extends from the first end portion of said support member;
(C) a reinforcing member having first and second end portions, said first end portion of the reinforcing member extending from said support member over the first end portion of the sensor body and forming a tapered portion; and
(D) a sealing member for sealing the sensor body and the reinforcing member except for the gate portions of the first and second FETs.

7. The sensor device according to claim 6 wherein the film sensitive to a specified component of the solution contains a graft copolymer of a siloxane monomer and a comonomer other than a siloxane monomer which contains at least 1.5% by weight of siloxane groups, and a substance sensitive to said specified component of the solution.

8. The sensor device according to claim 7, wherein the comonomer is a nonionic monomer.

9. The sensor device according to claim 8, wherein the support member also acts as a reinforcing member.

* * * * *